(12) United States Patent
Butler et al.

(10) Patent No.: US 8,268,001 B2
(45) Date of Patent: Sep. 18, 2012

(54) FOLDABLE ORTHOPEDIC IMPLANT

(75) Inventors: Michael S. Butler, St. Charles, IL (US);
Kara A. Bucci, Palos Park, IL (US)

(73) Assignee: Life Spine, Inc., Hoffman Estates, IL (US)

( * ) Notice: Subject to any disclaimer, the term of this patent is extended or adjusted under 35 U.S.C. 154(b) by 0 days.

(21) Appl. No.: 12/258,705

(22) Filed: Oct. 27, 2008

(65) Prior Publication Data
US 2009/0112318 A1 Apr. 30, 2009

Related U.S. Application Data

(60) Provisional application No. 61/000,772, filed on Oct. 29, 2007.

(51) Int. Cl.
*A61F 2/44* (2006.01)

(52) U.S. Cl. .................................. 623/17.16

(58) Field of Classification Search .... 623/17.11–17.16, 623/1.11, 1.13, 1.15, 1.12; 606/246, 247; 220/6, 7, 4.29, 4.28
See application file for complete search history.

(56) References Cited

U.S. PATENT DOCUMENTS

| | | | |
|---|---|---|---|
| 3,675,808 A * | 7/1972 | Brink ............................ | 220/7 |
| 5,390,683 A | 2/1995 | Pisharodi | |
| 5,658,335 A | 8/1997 | Allen | |
| 5,658,337 A | 8/1997 | Kohrs et al. | |
| 5,844,036 A * | 12/1998 | Hughes ........................ | 524/494 |
| 6,039,761 A * | 3/2000 | Li et al. ...................... | 623/17.16 |
| 6,126,689 A | 10/2000 | Brett | |
| 6,176,882 B1 | 1/2001 | Biedermann et al. | |
| 6,371,989 B1 * | 4/2002 | Chauvin et al. ............ | 623/17.11 |
| 6,375,682 B1 | 4/2002 | Fleischmann et al. | |
| 6,409,766 B1 | 6/2002 | Brett | |
| 6,491,724 B1 | 12/2002 | Ferree | |
| 6,494,883 B1 | 12/2002 | Ferree | |
| 6,537,320 B1 | 3/2003 | Michelson | |
| 6,648,917 B2 | 11/2003 | Gerbec et al. | |
| 6,773,460 B2 | 8/2004 | Jackson | |
| 7,087,055 B2 | 8/2006 | Lim et al. | |
| 2004/0153156 A1 | 8/2004 | Cohen et al. | |
| 2004/0167625 A1 | 8/2004 | Beyar et al. | |
| 2005/0033437 A1 | 2/2005 | Bao et al. | |

(Continued)

FOREIGN PATENT DOCUMENTS

WO WO-2006/105437 10/2006

*Primary Examiner* — Eduardo C Robert
*Assistant Examiner* — Summer Kostelnik
(74) *Attorney, Agent, or Firm* — Foley & Lardner LLP

(57) ABSTRACT

An orthopedic implant such as a spinal implant is made from a elastic biocompatible material (e.g. polyetheretherketone or PEEK) to provide a hinge that allows portions of the orthopedic implant to be folded into a closed position and to inherently deploy into an open position upon release of a folding bias. Hence, the orthopedic implant can accommodate a minimally invasive surgical procedure since the orthopedic implant can be introduced into the disc space in the closed position through a small-diameter insertion tube and then deploy to a particular height once the implant is released from the insertion tube (i.e. from release of the folding bias). The present implant is preferably, but not necessarily, made by injection molded PEEK. In this manner, the implant components are molded in the open position to cause the open position to be its innate position or form, thus allowing the implant to self-deploy (self-expand) when it is released from the folding bias.

20 Claims, 4 Drawing Sheets

U.S. PATENT DOCUMENTS

| | | |
|---|---|---|
| 2005/0131536 A1 | 6/2005 | Eisermann et al. |
| 2005/0143827 A1 | 6/2005 | Globerman et al. |
| 2005/0228391 A1 | 10/2005 | Levy et al. |
| 2005/0283246 A1* | 12/2005 | Cauthen et al. ............ 623/17.16 |
| 2006/0015136 A1* | 1/2006 | Besselink ..................... 606/200 |
| 2006/0095136 A1 | 5/2006 | McLuen |
| 2006/0189999 A1 | 8/2006 | Zwirkoski |
| 2006/0224241 A1* | 10/2006 | Butler et al. ............... 623/17.15 |
| 2007/0049931 A1* | 3/2007 | Justis et al. .................... 606/61 |
| 2007/0073398 A1* | 3/2007 | Fabian et al. ............. 623/17.11 |

* cited by examiner

FOLDABLE ORTHOPEDIC IMPLANT

RELATED APPLICATIONS

This patent application claims the benefit of and/or priority to U.S. provisional patent application Ser. No. 61/000,772 filed Oct. 29, 2007, entitled "Foldable Orthopedic Implant" the entire contents of which is specifically incorporated herein by this reference.

BACKGROUND OF THE INVENTION

1. Field of the Invention

The present invention relates to orthopedic implants and, more particularly, to foldable orthopedic implants such as are used in minimally invasive surgery of which a spinal implant is a type.

2. Background Information

There are situations in orthopedic surgeries when it would be desirable to have an implant that would be self-deployable. One such orthopedic situation is with relation to the spine as related below.

The disc between vertebrae of a human spine may sometimes become damaged due to disease or injury, or may simply deteriorate due to age, defect or the like. With others, the vertebrae may become compressed or otherwise damaged for various reasons. In these and other cases the vertebrae can become too closely spaced anteriorly which causes an undesired abnormal curvature of the spine with respect to lordosis or kyphosis.

Because of this, surgery may be utilized to place one or more spinal spacers or interbody devices between adjacent vertebrae in order to provide proper spacing and/or orientation of the vertebrae. In some cases the spinal interbody device may be an artificial or prosthetic spinal disc that is designed to replace the existing spinal disc. In some cases the spinal interbody device is a device that supports and/or realigns the adjacent vertebrae relative to one another and which promotes fusion between the vertebrae. Bone fusion material is typically used with spinal implant devices in order to promote growth of the bone between the adjacent vertebrae to thereby create fusion of the adjacent vertebrae. The bone fusion material is placed about or in the spinal implant device.

When spinal interbody devices are used, it is desirable for them to engage as much surface of the bone of the vertebrae as possible to provide support to the bone and to thereby reduce the likelihood of subsidence of the device into the vertebrae or bone resulting from contact pressure of the spinal interbody device against bone surfaces. Subsidence can occur since part of the bone is somewhat spongy in nature, especially near the centers of the adjacent vertebrae.

The configuration and/or structure of spinal interbody devices functions to provide support, spacing and orientation between the two adjacent vertebrae. Therefore, one or more dimensions of the implant device, such as height or intervertebral spacing (i.e. the distance between an upper vertebral surface of a lower vertebra of the vertebrae pair to a lower vertebral surface of an upper vertebra of the vertebrae pair), must correspond to a desired intervertebral spacing. This dimension may be relatively large. Since it is desirable to employ minimally invasive surgical procedures (minimally invasive surgery or MIS) when possible, the user of spinal implant, spinal implant devices of certain sizes cannot be used. Therefore, spinal implant devices have been developed that are small enough to be implanted using MIS and which can then be expanded after implantation. These devices, however, require the surgeon to mechanically expand the implant device once implanted. This is not easy when using MIS. Mechanically expandable spinal implant devices are also deficient in other areas.

Accordingly, there presently exists a need for improved spinal implants, particularly for MIS use. Moreover, there presently exists a need for improved orthopedic implants in general.

SUMMARY OF THE INVENTION

According to one aspect of the present invention, there is provided an orthopedic implant and a process of forming the orthopedic implant having an elastic hinge. The elastic hinge connects two portions of the orthopedic implant such that the two portions fold or bend relative to one another. The orthopedic implant is preferably, but not necessarily, molded from a biocompatible elastic plastic.

The present hinged orthopedic implant is preferably, but not necessarily, formed of the biocompatible elastic material PEEK (polyetheretherketone). Other biocompatible elastic plastics, thermoplastics, polymers and/or the like may be used. The present orthopedic implant is preferably formed by injection molding wherein an innate position corresponding to an expanded, opened or deployed position may be created.

The present hinged orthopedic implant may be one component of a multi-component orthopedic implant or the hinged orthopedic implant may be formed as a single component.

Each hinge of the orthopedic implant is formed by providing a folding point of a reduced thickness area of the PEEK material (i.e. elastic biocompatible material) between one portion and another portion such as a base and panels, flaps or portions of the orthopedic implant. These areas or strips form elastic hinges that allow the panels, flaps or portions to elastically bend relative to the base to define a closed, deformed or biased position and to inherently spring or deploy into an open position upon release of a folding bias.

In this manner, a single or multi-part orthopedic implant can be made to accommodate a minimally invasive surgical procedure since it can be introduced into in a folded position through a small-diameter insertion tube and then be self-deployable into a particular height once the implant is released from the insertion tube (i.e. the folding bias).

In accordance with the principles of the present invention, implant components are molded in an open position to cause the open position to be its innate position or form, thus allowing the implant to self-deploy (self-expand) when it is released from a folding or body-deforming bias.

In one form, the present invention provides a spinal implant that is made from a biocompatible elastic material such that one or more foldable or bendable portions thereof return to an original expanded position from a folded or bent position upon release of the folded/bent portions from a folding bias. The implant incorporates hinges connecting portions of the implant to a base thereof.

In another form, the present invention provides a spinal implant incorporating elastically hinged portions that return to an innately open position from a deformed position upon release from a deformation bias.

Additionally, an implant is provided that incorporates a plurality of elastic spinal implants as described herein to define a spinal interbody device. In this form, a plurality of elastic spinal implants are axially stacked upon on another and held together on and by an axial form.

BRIEF DESCRIPTION OF THE DRAWINGS

The above mentioned and other features, advantages and objects of this invention, and the manner of attaining them, will become apparent and the invention itself will be better understood by reference to the following description of an embodiment of the invention taken in conjunction with the accompanying drawings, wherein.

Like reference numerals indicate the same or similar parts throughout the several figures.

A detail of the features, functions and/or configuration of the components depicted in the various figures will now be presented. It should be appreciated that not all of the features of the components of the figures are necessarily described. Some of these non discussed features as well as discussed features are inherent from the figures. Other non discussed features may be inherent in component geometry and/or configuration.

DETAILED DESCRIPTION OF AN EMBODIMENT OF THE INVENTION

It should be appreciated that the principles of the present invention are applicable to all types of orthopedic implants wherein it is desired to provide an elastic or "living" hinge between components, portions or parts thereof. However, for simplicity of illustration, only one such orthopedic implant, i.e. a spinal implant, having an elastic hinge in accordance with the present principles will be shown and described, it being understood that the spinal implant is representative of all such types of orthopedic implants wherein it is desired to provide an elastic or living hinge. More particularly, the orthopedic implant shown in FIGS. 1-4 is one component of a multi-component orthopedic implant wherein the components are axially stacked with like components.

Referring to FIGS. 1-4 there is depicted an exemplary spinal implant or device and, particularly, a spinal intervertebral or interbody device or implant, generally designated 10, fashioned in accordance with the present principles. It should be appreciated that the implant 10 represents one embodiment of a spinal implant that utilizes one or more elastic properties of a biocompatible material to create a self deploying or self expanding implant. The implant 10 is shown in an open position in FIGS. 3 and 4, and in a closed position in FIGS. 1 and 2. The open position is the innate position of the implant. The closed position is a position achieved under stress or deformation of one or more portions of the implant 10 such as by folding, bending or binding (i.e. a deformation bias) the one or more portions of the implant 10. Because of its elasticity the implant will return to its innate state (i.e. its open, deployed or expanded position) after deformation biasing of its one or more portions has ceased.

Figure 3:
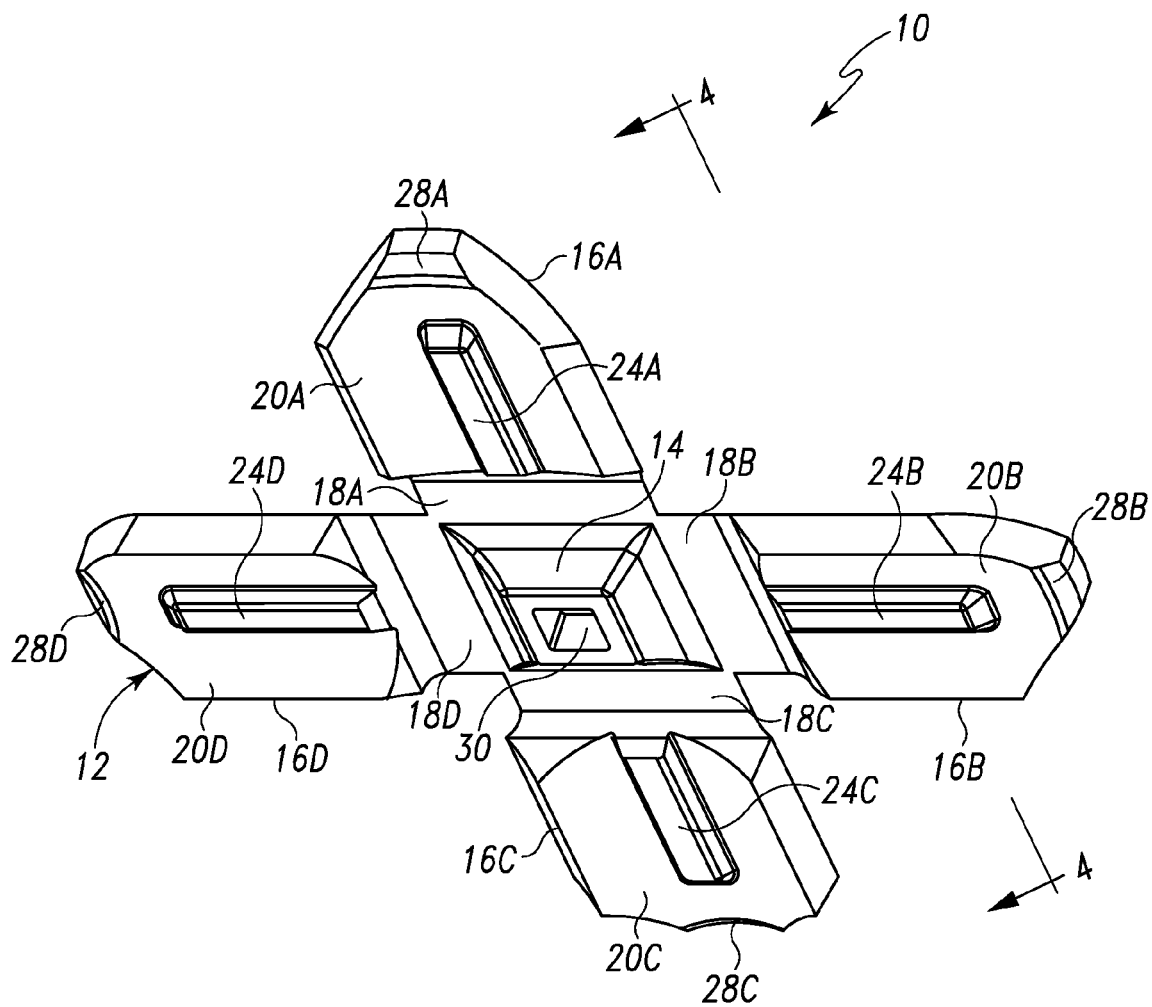
FIG. 3 is a bottom perspective view of the foldable spinal implant of FIGS. 1 and 2 shown in a deployed or open position.
Figure 4:
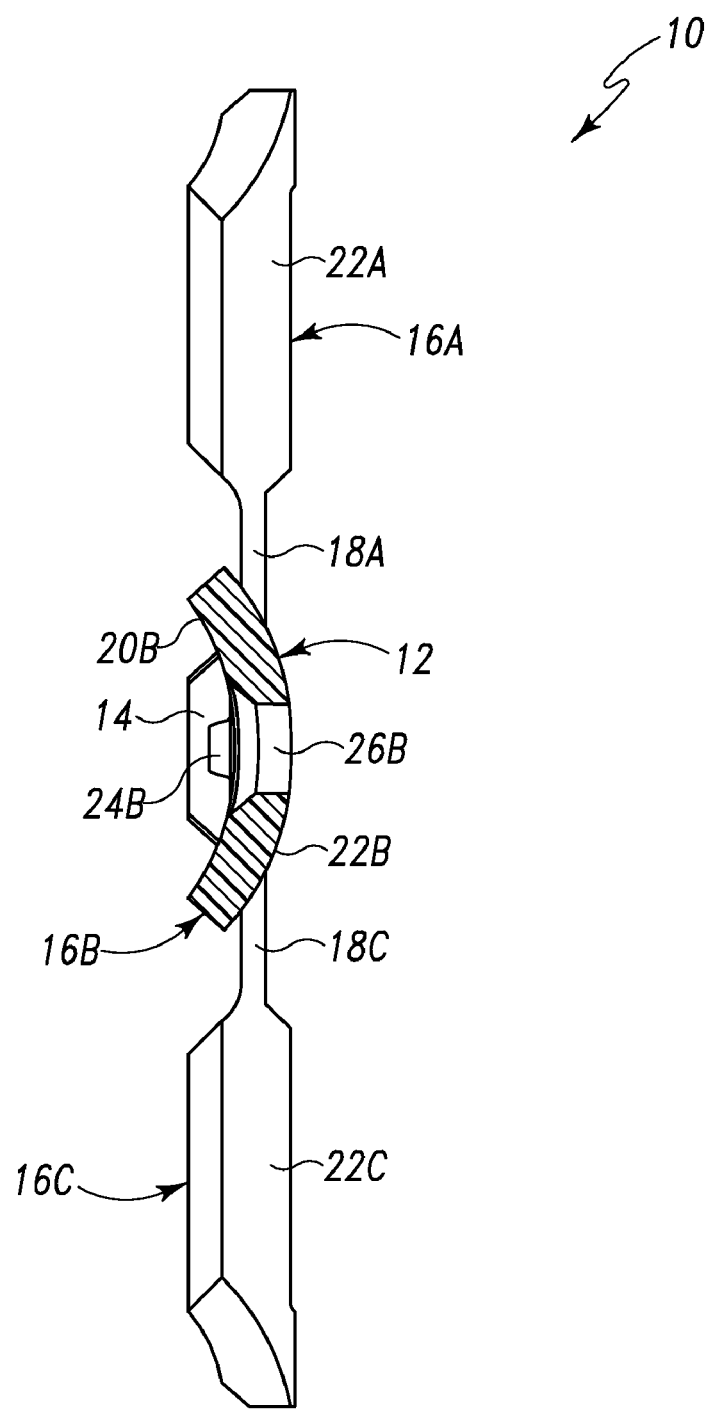
FIG. 4 is a side view of the foldable spinal implant of FIG. 3 taken along line 4-4 thereof.

The implant 10 is defined by a body 12 that is made of an elastic, biocompatible material such as PEEK (polyetheretherketone) but may be formed from other biocompatible thermoplastics, polymers or the like as appropriate. The body 12 is preferably, but not necessarily, injection molded, however, other techniques may be used. The body 12 is molded into a desired expanded or deployed state (i.e. its innate form or open position) such as shown in FIGS. 3 and 4. The body 12 is sized to be received in an insertion tube such as is used in minimally invasive surgery or surgical techniques. Of course, the body 12 may be sized accordingly. As such, the body 12 may be fabricated in various sizes to accommodate various requirements and/or applications.

Figure 1:
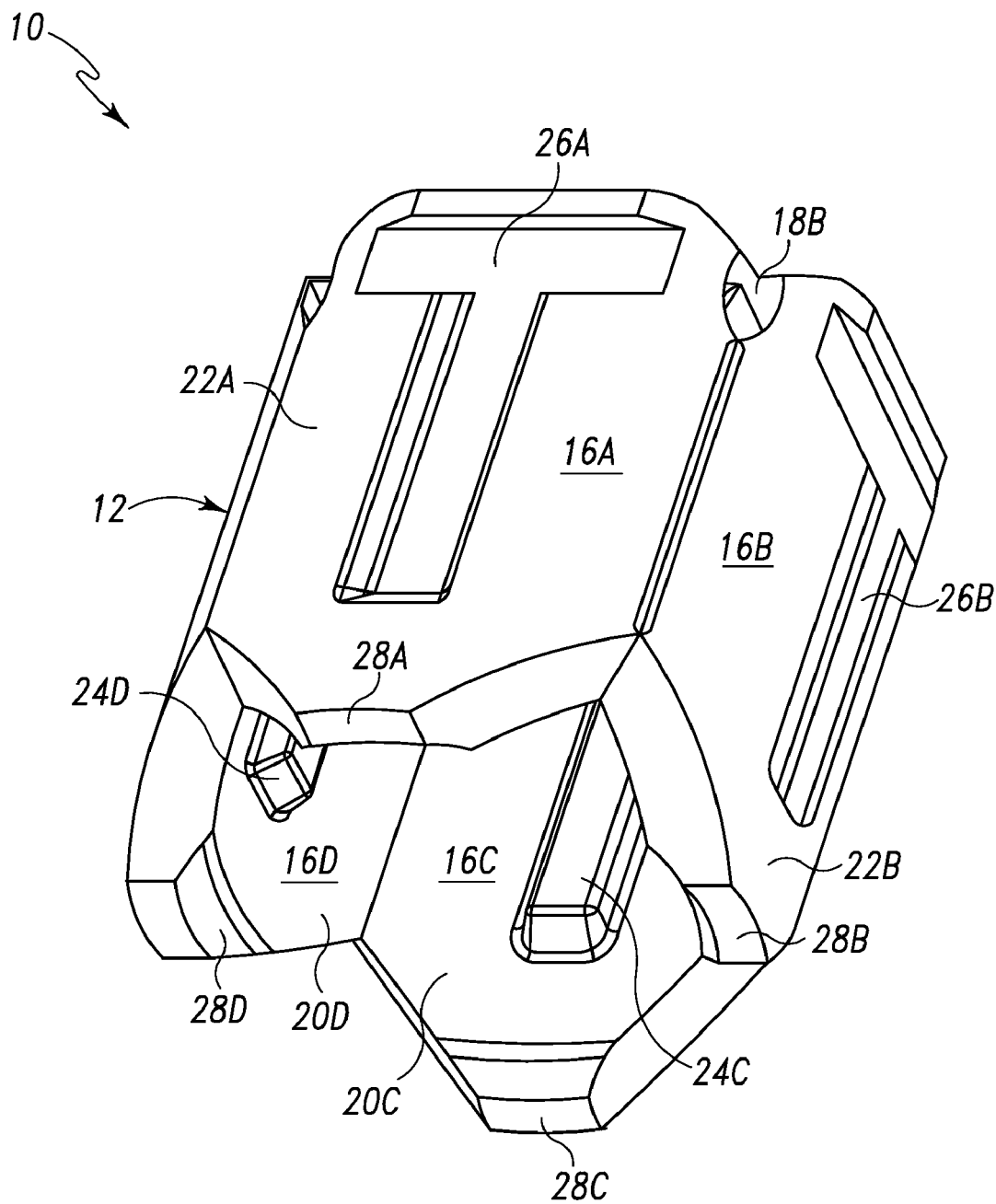
FIG. 1 is a bottom perspective view of an embodiment of a foldable spinal implant shown in a folded or closed position.
Figure 2:
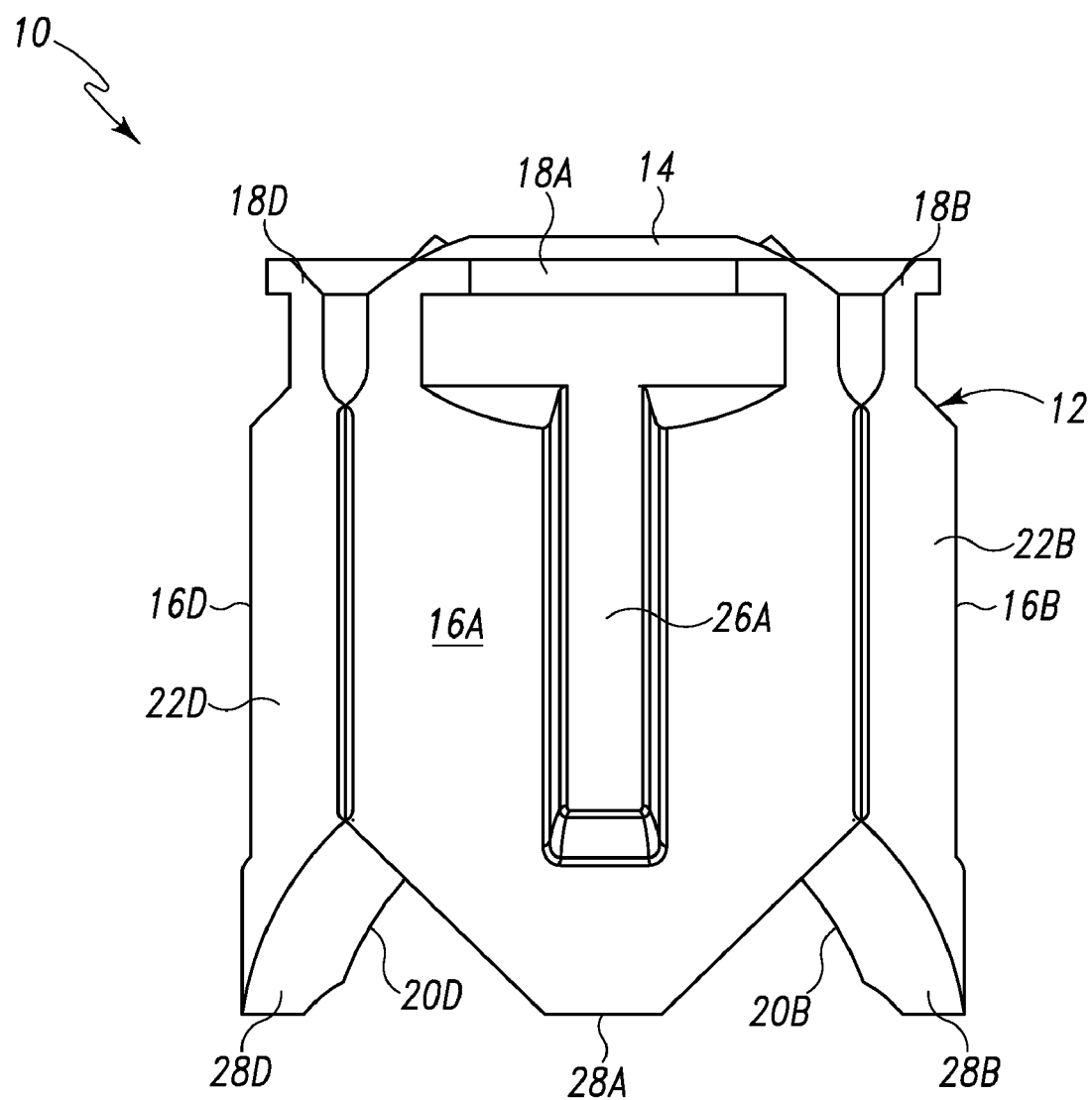
FIG. 2 is a side view of the foldable spinal implant of FIG. 1.

The body 12 has a base 14 defining a central portion of hub with a bore 30 extending through the base 14. While the base 14 is shown as being rectangular it should be appreciated that the base may take other shapes as desired and/or is appropriate. The body further includes a plurality of panels, sections, portions, leaves, petals or the like 16 that extend radially from the base 14. The implant 10 is shown with four (4) panels 16a, 16b, 16c and 16d it being understood that the implant may have more or less panels. Each panel 16 (i.e. panels 16a, 16b, 16c and 16d) is connected to the base 14 via a hinge or hinge structure 18. Each hinge 18 is defined by a strip of the elastic material that extends from an edge of the base 14 to a panel 16. Each strip is reduced in thickness relative to the other portions of the implant and/or particularly is of a thickness that allows elastic bending thereof without breaking in order to form an elastic or "living" hinge (i.e. hinges 18a, 18b, 18c and 18d) between the panels (16a, 16b, 16c and 16d) and the base 14. As seen in FIGS. 1 and 2, the hinges 18a, 18b, 18c and 18d allow their respective panels 16a, 16b, 16c and 16d to fold inward toward an axis of the base 14 to thereby define a closed or biased position. Once the deformation bias is removed, the closed position of FIGS. 1 and 2 automatically (through the elasticity of the material) becomes the open, deployed, innate or expanded position of FIGS. 3 and 4.

The implant 10 is particularly, but not necessarily, designed for use as one implant component of a plurality of implant components of the same configuration and properties as implant 10 to form a spinal interbody device. In this configuration (not shown herein), the plurality of implant components 10 are axially arranged to form an axial stack of implant components. In this manner, bases 14 of adjacent bodies 12 axially unite while panels 16 of one body 12 unite with panels 16 of an adjacent body 12. The panels 16 are configured via their hinges 18 to bend together and around one another when axially stacked and biased. The number of implant components 10 may vary as desired. The stack of implant components 10 may be retained by axial form, pole or the like.

Each panel 16 is thus configured to engage a like panel of an adjacent implant component 10. The configuration of a panel 16 provides for rotational stability of one panel 16 relative to a panel 16 of an adjacent implant component 10 and the positive axial joining thereof. It should be appreciated that the configuration of a panel 16 may differ from that shown in the figures. Each panel 16 includes a curved concave inner surface 20 (i.e. 20a, 20b, 20c and 20d) and a curved convex outer surface 22 (i.e. 22a, 22b, 22c and 22d). A ridge 24 (i.e. 24a, 24b, 24c and 24d) is formed on each inner surface (i.e. 20a, 20b, 20c and 20d). The panel ridge 24 extends radially from the base 14 and along the inner surface 22 thereof. A channel 26 (i.e. 26a, 26b, 26c and 26d) is formed on each outer surface (i.e. 22a, 22b, 22c and 22d) and is configured to receive a panel ridge 24 of an adjacent panel 16.

It should also be appreciated that while each panel 16 is formed with a square tip 28, other configurations are contemplated. Likewise, each panel 16 is formed with a beveled or angled edge. The angle of the edges aids in insertion of a folded implant through an insertion tube.

While the invention has been illustrated and described in detail in the drawings and foregoing description, the same is to be considered as illustrative and not restrictive in character, it being understood that only a preferred embodiment has been shown and described and that all changes and modifications that come within the spirit of the invention are desired to be protected.

What is claimed is:

1. An orthopedic implant comprising:
   a base;
   a plurality of panels, each panel having a first end, a second end, a first major surface, and a second major surface opposite the first major surface, the first major surface having a ridge and the second major surface having a channel and configured to receive the ridge on the first major surface of an adjacent panel; and
   a plurality of hinges formed integrally between the base and the first ends of the panels whereby the panels elastically bend relative to the base to define a folded position upon application of a folding bias and an unfolded position upon release of the folding bias;
   wherein the each of the panels is curved such that the first major surface is concave and the second major surface is convex.

2. The orthopedic implant of claim 1, wherein the base, the second portion and the hinge are formed from a biocompatible plastic.

3. The orthopedic implant of claim 2, wherein the biocompatible plastic comprises PEEK.

4. The orthopedic implant of claim 2, wherein the base, each of the panels, and the hinge are formed by injection molding wherein an innate position corresponding to the open position is created.

5. The orthopedic implant of claim 1, wherein the hinge has a linear axis of rotation and is formed by a reduced thickness area.

6. The orthopedic implant of claim 1, wherein the plurality of panels comprises four panels.

7. The orthopedic implant of claim 1, wherein each of the panels has a first lateral edge and a second lateral edge and the first major surface and the second major surface extend between the first lateral edge and the second lateral edge.

8. The orthopedic implant of claim 7, wherein the first lateral edge comprises a beveled surface and the second lateral edge comprises a beveled surface configured to engage beveled surfaces of adjacent panels which are hingedly coupled to the base.

9. A method of making an orthopedic implant comprising the steps of:
   forming a base;
   forming a plurality of curved panels, each with a concave first major surface and a convex second major surface, the first major surface having a ridge and the second major surface having a channel and configured to receive the ridge on the first major surface of an adjacent panel; and
   forming elastic hinges between the base and each of the curved panels, the elastic hinges configured to allow elastic bending of each of the corresponding curved panels relative to the base between a folded position upon application of a folding force and an unfolded position upon release of the folding force, wherein the each panel is biased toward the unfolded position.

10. The method of claim 9, further comprising the step of providing a biocompatible material comprising a biocompatible plastic.

11. The method of claim 10, wherein the biocompatible plastic comprises PEEK.

12. The method of claim 9, wherein the base, each of the curved panels, and the elastic hinges are formed by injection molding wherein an innate position corresponding to the open position is created.

13. The method of claim 9, wherein the elastic hinges are formed by a reduced thickness area.

14. The method of claim 9,
   wherein the step of forming the plurality of curved panels further comprises providing each with a first beveled lateral edge and a second beveled lateral edge;
   wherein the second beveled lateral edge of a first curved panel engages the first beveled lateral edge of second curved panel when the first and second panels are in their folded positions.

15. An orthopedic implant comprising:
   a first implant comprising a base and a plurality of panels hingedly coupled to the base and pivotal between an open position and a closed position, each of the panels having a first major surface and a second major surface, the first major surface having a ridge extending therefrom, the second major surface having a channel therein, wherein a first pair of opposing panels are biased to expand in a first direction and a second pair of opposing panels are biased to expand in a second direction perpendicular to the first direction;
   a second implant comprising a base and a plurality of panels hingedly coupled to the base and pivotal between an open position and a closed position, each of the panels having a first major surface and a second major surface, the first major surface having a ridge extending therefrom, the second major surface having a channel therein, wherein a first pair of opposing panels are biased to expand in a first direction and a second pair of opposing panels are biased to expand in a second direction perpendicular to the first direction;
   wherein the ridges on the panels of the first implant engage the channels on the panels of the second implant when the first and second implants are in the open position and axially arranged adjacent each other.

16. The orthopedic implant of claim 15, wherein the engagement of the ridges and channels of adjacent panels of the first and second implants is configured to provide rotational stability of the adjacent panels.

17. The orthopedic implant of claim 16, wherein the panels are curved such that the first major surface is concave and the second major surface is convex.

18. The orthopedic implant of claim 16, wherein the adjacent panels of the first and second implants are configured to bend together and around one another when the first and second implants are axially stacked and pivoted toward the closed positions.

19. The orthopedic implant of claim 18, wherein the open position is when the hinges are in an unbiased condition and the closed position is when the hinges are in a biased condition.

20. The orthopedic implant of claim 18, wherein the panels are generally parallel to the base when in the open position.

* * * * *